US006802854B1

(12) United States Patent
McFarland

(10) Patent No.: US 6,802,854 B1
(45) Date of Patent: Oct. 12, 2004

(54) MODULAR, KNOCK-DOWN TANNING BED

(75) Inventor: Kevin Mark McFarland, Fair Oaks, CA (US)

(73) Assignee: Indoor Sun Systems, Inc., Rancho Cordova, CA (US)

( * ) Notice: Subject to any disclaimer, the term of this patent is extended or adjusted under 35 U.S.C. 154(b) by 0 days.

(21) Appl. No.: 09/431,636

(22) Filed: Nov. 1, 1999

(51) Int. Cl.$^7$ .............................................. A61N 5/006
(52) U.S. Cl. ............................ 607/91; 607/88; 607/94; 250/498.1; 250/504 R
(58) Field of Search .................. 607/88, 90, 91–94, 607/96; 250/493.1, 498.1, 504 R; 5/4–6

(56) References Cited

U.S. PATENT DOCUMENTS

| | | | | |
|---|---|---|---|---|
| 4,600,009 A | * | 7/1986 | Kramer et al. | 128/396 |
| 4,683,887 A | * | 8/1987 | Kramer et al. | 128/376 |
| 4,881,548 A | * | 11/1989 | Kramer | 128/376 |
| 4,918,319 A | * | 4/1990 | Kruithof | 250/504 R |
| 4,984,571 A | * | 1/1991 | Springer, Jr. et al. | 128/371 |
| 4,993,091 A | * | 2/1991 | Drapper et al. | 5/487 |
| 5,383,916 A | * | 1/1995 | Brown | 607/91 |
| 5,725,565 A | * | 3/1998 | Smith | 607/88 |
| 6,139,568 A | * | 10/2000 | Doty | 607/91 |

OTHER PUBLICATIONS

Montego Bay brochure, "Building a better tanning bed; 3200 Legend", Tanning Tchnology, (1996).*
Amerisun product catalog, "Amerisun 1997 Catalog", pp. 30–36 and 44, 1997.
ASM, Inc. product brochure, "Hapro Brings Color to Life with ProSun and Luxura", entire brochure, date unknown.
Body Quest product brochure, "Introducing the Body Crafter", entire brochure, date unknown.
Creative Marketing Concepts, Inc., "Owners Manual, Operation and Assembly Instructions, Warranty Information for Sun Capsule VHR®, The Ultimate Tanning Machine", entire manual, date unknown.
Dr. Kern product brochure, "Blue Dream", entire brochure, date unknown.
Ergoline product brochure, "Classic 450 TurboPower", entire brochure, 1999.
ETS, Inc. catalog, "1995 SunQuest® Wolff® Systems", entire catalog, 1995.
Health and Fitness Products of America, Inc. product brochure, "Sportarredo", entire brochure, date unknown.
Hex product brochure, "Hex Tanning Systems", entire brochure, 1995.
High–Tech–Bräuner product brochure, "Delight", entire brochure, date unknown.
High–Tech–Bräuner product brochure, "Magic", entire brochure, date unknown.
High–Tech–Bräuner product brochure, "Space", entire brochure, date unknown.
High–Tech–Bräuner product brochure, "Super", entire brochure, date unknown.
High–Tech Bräuner product brochure, "Ein Konzept", entire brochure, date unknown.
Indoor Sun Systems, Inc. operations manual, "Operation and Instructions for the use of your TanAmerica", entire manual, 1992.

(List continued on next page.)

Primary Examiner—Linda C. M. Dvorak
Assistant Examiner—A. Farah
(74) Attorney, Agent, or Firm—Bernhard Kreten and Associates

(57) ABSTRACT

A tanning bed formed a plurality of modular components that are integrated in a knock-down fashion that allows easy shipment of tanning beds in less than complete form, but allows the rapid assembly without the need of special training or tools.

3 Claims, 8 Drawing Sheets

OTHER PUBLICATIONS

Klafsun–Sunrite product brochure, "Cosmos", entire brochure, date unknown.
Klafsun–Sunrite product brochure, "Pro 3000", entire brochure, date unknown.
Klafsun–Sunrite catalog, "Klafsun–Sunrite Tanning Equipment & Accessories Catalog", entire catalog, date unknown.
Looking Fit Magazine, "Chicago 10th Anniversary Pre–Show Planner", entire magazine, Sep. 1999.
Montego Bay product brochure, "Montego Bay Premium Tanning Equipment", entire brochure, 1996.
PC Marketing product brochure, Der groBe Bär, entire brochure, date unknown.
Professional Tan product brochure, "Indoor Tanning Guide", pp. 64–71, 1999.
Puretan product brochure, "Quality Through Experience . . . Gauranteed!", entire brochure, date unknown.
QDM, Co., Inc. product brochure, "Original Dr. Müller, Solar System", entire brochure, 1994.
QDM, Co., Inc. product brochure, "The Ultimate Tanning Experience" entire brochure, 1995.
SonnenBräune product brochure, "Tanning for today's lifestyles", entire brochure, 1995.
Sun Industries product brochure, "Cyber–Dome", entire brochure, date unknown.
Sun Industries product brochure, "Think Big", entire brochure, date unknown.
Sun Industries product brochure, "Triangular UV–Wavelength Integration", entire brochure, date unknown.
Sun Industries product brochure, "Sun Industries Year 2000", entire brochure, 1999.
Sun Industries Magazine, "Exploring the Profit Potential of the Sun", entire magazine, vol. 4, date unknown.
Sun Industries product brochure, "Sun Business Update", entire brochure, date unknown.
Sun Industries product brochure, "Indoor Tanning Procedures and Guidelines", entire brochure, date unknown.
Sun Capsule product brochure, "Perfect Ten", entire brochure, 1997.
Sunal catalog, "Find Your Place in the Sun", entire catalog, 1995.
Sunal product brochure, "The Name in Tanning", entire brochure, date unknown.
Sunliner product brochure, "It's What's Inside that Counts", entire brochure, date unknown.
Sun Systems catalog, "Sun Systems", entire catalog, 1997.
Sybaritic, Inc. product brochure, "Alpha Health Environment Capsule, Look Better, Feel Better, Live Better", entire brochure, date unknown.
Sybaritic, Inc. product brochure, "Sunspectra 9000", entire brochure, date unknown.
Sun Industries, "Specifications for Model Nos. R–26B and R32B", entire specification, Mar. 1997.
Sun Industries product brochure, "Solid Steel . . . Solid Steal!", entire brochure, date unknown.
Sun Industries product brochure, "Sundash–2 Genesis", entire brochure, date unknown.
Sun Industries product brochure, "Suntana Passport 16", entire brochure, 1997.
Sun Industries product brochure, "The Ultimate Home Tanning System", entire brochure, date unknown.
Ultrabronz USA Inc., "High Pressure Tanning", entire brochure, date unknown.
UltraSun Professional product brochure, "Control the Elements", entire brochure, date unknown.
UltraSun Professional product brochure, "Control the Elements", entire brochure, date unknown.
UltraSun Professional product brochure, "Sweet Deal from Mother Nature" entire brochure, date unknown.
Vitasun product brochure, "High Pressure, Vitasun Technology" entire brochure, date unknown.

* cited by examiner

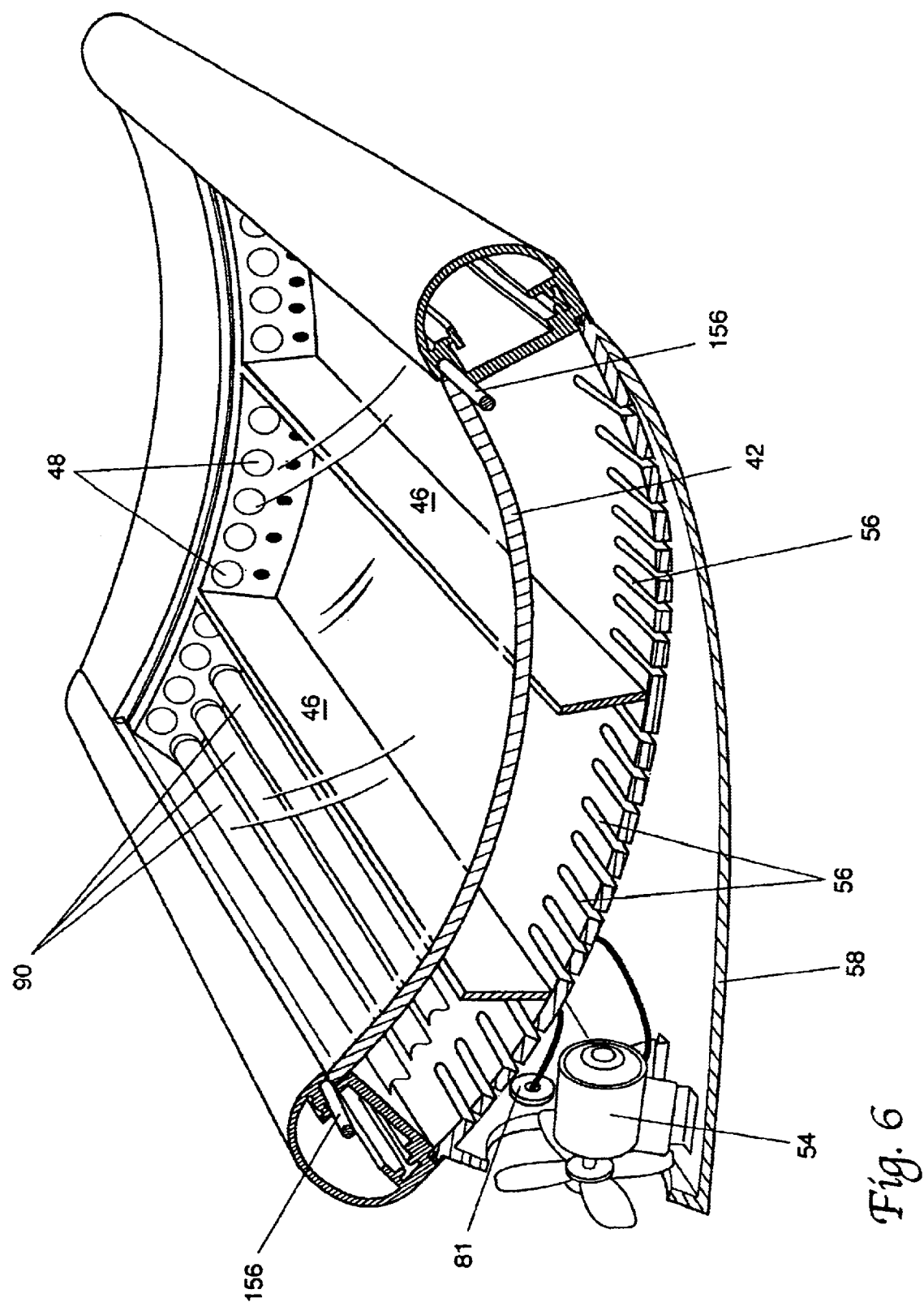

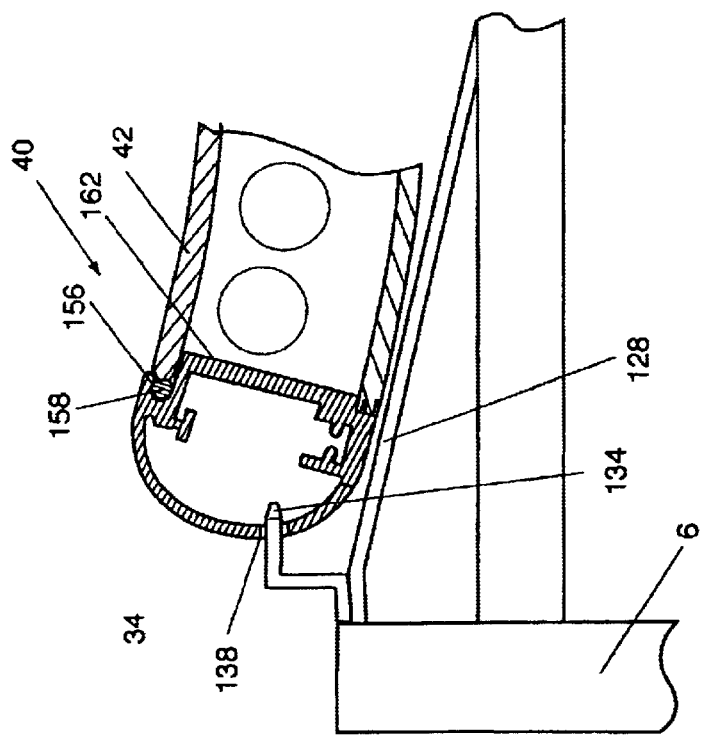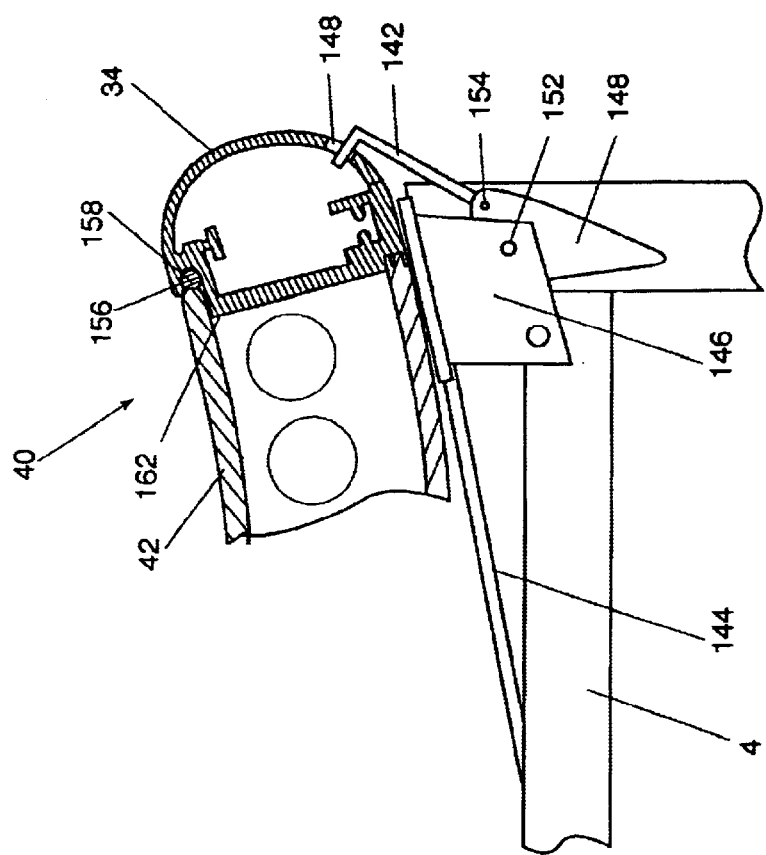

US 6,802,854 B1

MODULAR, KNOCK-DOWN TANNING BED

FIELD OF THE INVENTION

The instant invention relates generally to tanning beds and more particularly to tanning beds which can be assembled from modular components without the need for special tools.

BACKGROUND OF THE INVENTION

Commercial tanning beds are presently somewhat cumbersome structures both because of their bulk and weight and because of the traditional manufacturing techniques utilized in fabrication. Most structures are "clam shell" in configuration having a substantial base upon which a person seeking a tan is to lie and a counter-balanced cover moves from an open to a closed position directly overlying the person on the bed so that both sides of a person can be tanned simultaneously.

When conventional prior art beds have to be installed in a new location, they usually require special handling by trained personnel due to their cumbersome and bulky nature and because any on-site installation usually entails manipulative techniques outside the skill level of a typical prospective tanning bed owner or the owner's employees.

For example, the ballast which provides resistance that stabilizes the current in the circuit for the tanning ultraviolet lamps have been hard wired. Therefore wiring is a time consuming, tedious project requiring factory installation because it is outside the purview of all people except an experienced installer.

In addition, the structure of the tanning bed itself has historically been shipped as a monolith because the counter-balancing of the overlying tanning cover requires winches or springs which are not easy to set up outside of the manufacturing environment. Thus, the base portion and the cover itself normally travels as an integrated unit which makes shipping and deployment at the ultimate site difficult.

The prior art listed on Form PTO 1449 appended hereto reflects the state of the art of which applicant is aware and is included herewith to discharge applicant's acknowledge duty to disclose relevant prior art. It is stipulated, however, that none of these references teach singly nor render obvious when considered in any conceivable combination the nexus of the instant invention as disclosed in greater detail hereinafter and particularly claimed.

SUMMARY OF THE INVENTION

The instant invention addresses the foregoing problems by the provision of a tanning bed structure formed from a plurality of modules which collectively define discrete components of the tanning bed. These modules are readily interconnected without the need for specialized tools. Because they have been partitioned into easy to handle sizes, they can be more readily shipped to remote sites and then assembled for utilization.

The instant invention also provides these modules with a variety of knock-down coupling instrumentalities for assembling the components into an operational tanning bed. By making the interconnectablity of the relatively small number of components easy to perform, a tanning bed can be assembled or repaired in a short amount of time. Similarly, should the tanning bed need to be moved to another site, this too can be performed with a minimal skill level and relatively quickly.

The structure according to the instant invention also lends itself to rapid and facile maintenance. Because the ultraviolet tubes which provide the tanning require periodic replacement, it is desirable that access to the tubes can be afforded with minimal down time and simplicity so that relatively unskilled people can provide the maintenance to keep the beds operational. Access to the bulbs and their associated ballast is readily provided to achieve these aims. As a consequence of all these features, the instant invention addresses a long felt yet heretofore unsatisfied need in the industry.

OBJECTS OF THE INVENTION

Accordingly, it is a primary object of the instant invention to provide a new and novel tanning bed.

A further object of the present invention is to provide a device as characterized above which is modular in nature, formed from a plurality of components which lend themselves to ready assembly by means of a knock-down coupling regime.

A further object of the present invention is to provide a device as characterized above which is extremely easy to install, lends itself to ready shipment and can be maintained by relatively unskilled personnel.

A further object of the present invention is to provide a device as characterized above lends itself to the economies of scale of mass production and is extremely safe to use.

Viewed from a first vantage point, it is an object of the present invention to provide a tanning bed wherein a plurality of modules collectively define components of said tanning bed and includes a knock-down coupling means for assembling said components into an operational tanning bed.

These and other objects will be made manifest when considering the following detailed specification when taken in conjunction with the appended drawing figures.

BRIEF DESCRIPTION OF THE DRAWINGS

FIG. 6 is a sectional view of the bench, the canopy being similar.

FIG. 7 is a sectional view of one bench restraint.

FIG. 8 is a sectional view of another bench restraint.

DESCRIPTION OF PREFERRED EMBODIMENTS

Figure 1:
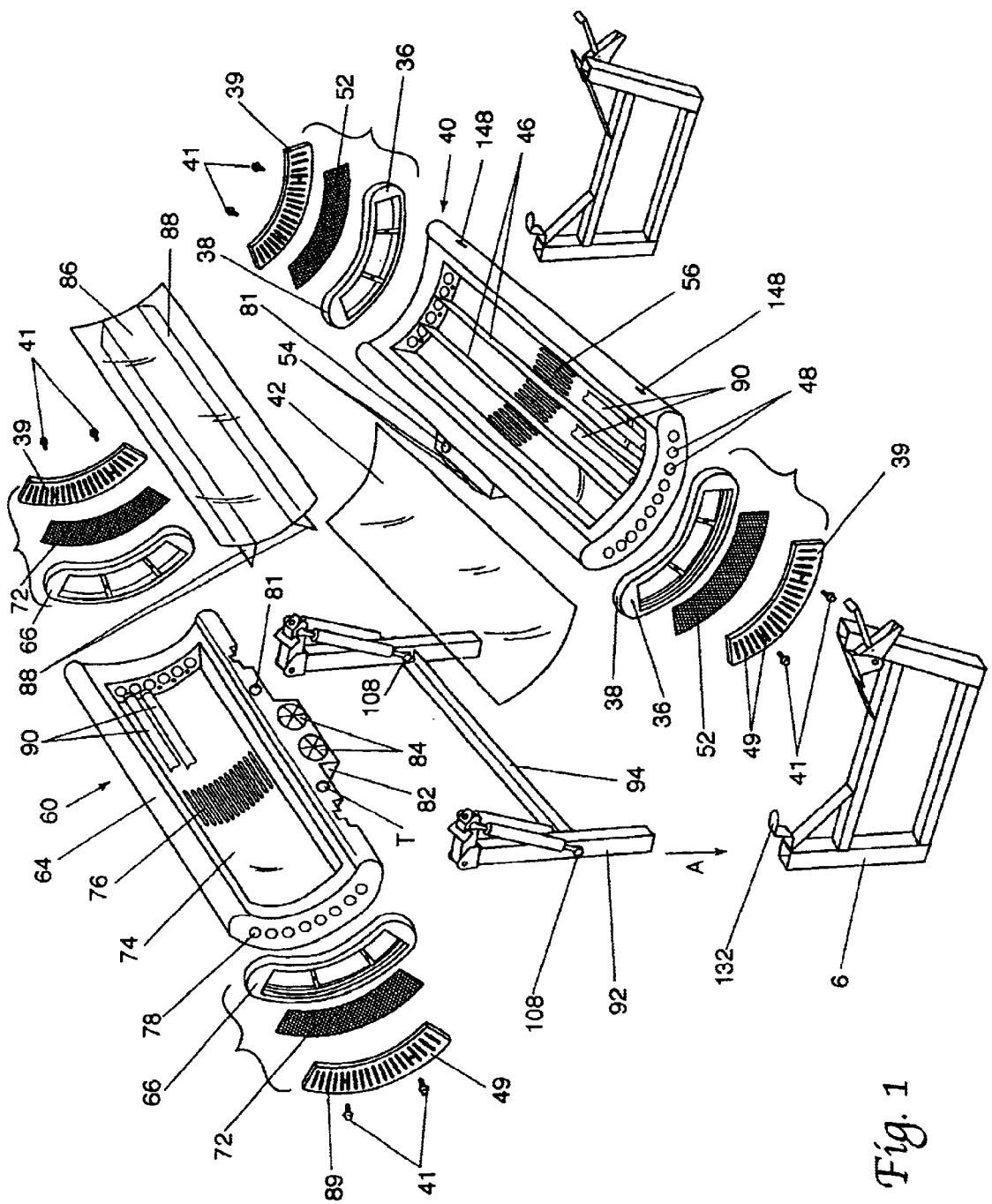
FIG. 1 is an exploded parts perspective view of the apparatus according to the present invention.

Referring to the drawings, wherein like reference numerals denote like parts, reference numeral 10 is directed to the tanning bed according to the present invention.

Figure 5:
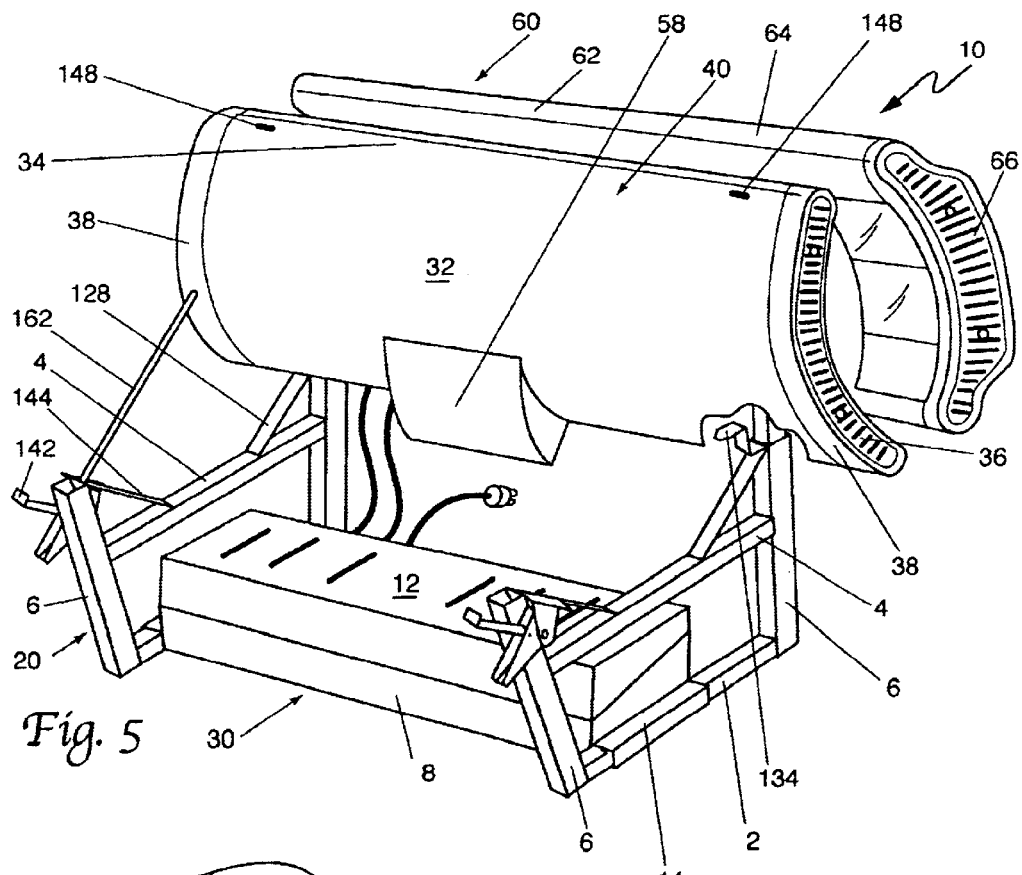
FIGS. 5 and 5A are perspective views detailing: the installation of the bench and canopy onto the tanning bed supports and access to the ballast housing, respectively.

Referring first to FIG. 5, the tanning bed 10 generally includes a pair of spaced bench supports 20 having a ballast housing 30 interposed therebetween and fixed thereto. The bench supports 20 cradle a bench 40 in removable, overlying relationship thereto. A canopy 60 is hinged to the bench 40 by removable attachments means to be described.

Each bench support 20 includes a lower horizontal member 2 and a longer upper horizontal member 4 which are interconnected by means of upwardly and outwardly diverging legs 6. The pair of bench supports 20 collectively define cradles upon which the bench 40 is to reside. The two bench supports 20 are secured in spaced parallel relationship by means of the ballast tray assembly 30. The ballast tray assembly 30 includes a lower tray 8 and an upper covering 12 within which the ballast modules are housed. Each opposite end of the ballast tray assembly includes an outwardly and downwardly projecting L shaped leg 14 on the lower tray 8 which overlies and grasps the horizontal legs 2 to fix the spaced relationship of the bench supports 20.

Figure 2:
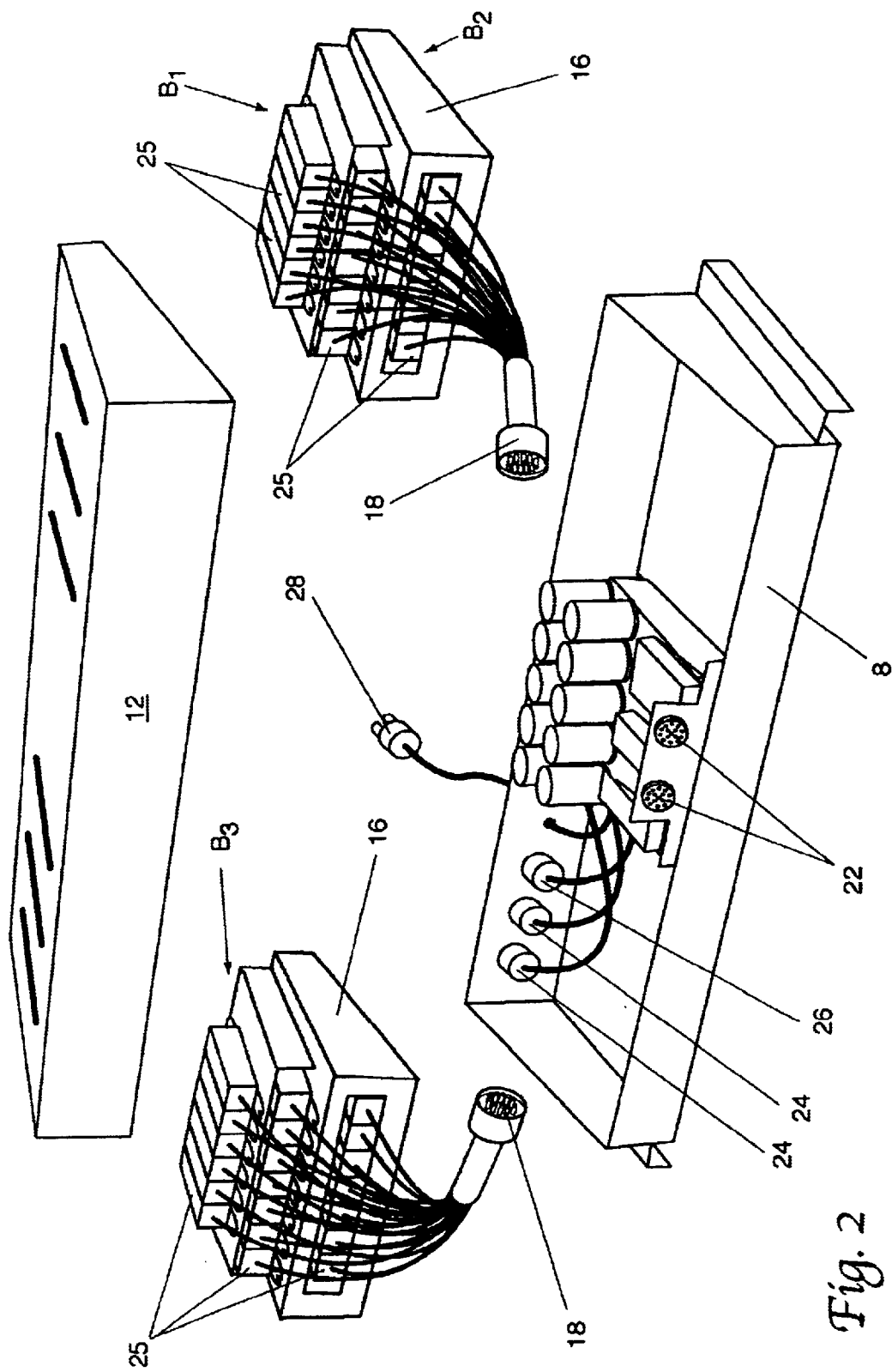
FIG. 2 details the modular components for the ballast assembly according to the present invention.

FIG. 2 shows ballast tray 8 in greater detail. An interior is provided in the open topped tray that includes first and second ballast units 16 at opposed extremities along the length of the tray 8. The ballast units are modular in construction and includes a plurality of wires terminating in plugs 18 each of which are received within appropriate sockets 22 and then through appropriate circuitry to outlets 24 which respectively power the bench illumination and canopy illumination 90. A timer outlet 26 leads to a timer T (FIG. 1) to control the amount of time that the tanning bed 10 is to remain on. The whole device 10 includes an AC outlet 28 for electrical communication in a building. The cover 12 overlies the ballast units 16, circuitry and plug inputs 22 protected by the exterior of the ballast housing 30.

The ballast is formed from a plurality of ballast modules 25 commercially available from Cosmedico Licht GmBH, Germany. They are choke ballasts, part number 74135. The ballasts 25 are each wired in series with a plurality of series wired ultraviolet lights 90. By wiring both the ballast in series as well as the lights in series, all ballast modules contribute to control circuit parameters, especially current and hold it substantially constant. Three banks $B_1$, $B_2$, and $B_3$, of ballast are shown respectively connected to: face light arrays, bench light arrays and canopy light arrays to be described.

The bench 40 shown in FIGS. 1 and 5 is a substantially hollow construct having an arcuate contour with the concave portion facing upwardly to address the prospective tanner. The bench 40 includes an arcuate bottom wall 32 and a pair of long peripheral side walls 34 which terminate at arcuate end walls 36. The end walls 36 have an inwardly directed flange 38 to slip over the side walls 34 and the bottom wall 32. The end walls 36 also abut against an edge of the clear bed cover 42 to hold it in position. The end walls 36 support foraminous, removeable end caps 39 attached by fasteners 41.

Ultraviolet bulbs 90 are located within the bench 40, below the clear cover 42, and clusters of bulbs 90 are spaced from other clusters by fins 46 so that channel ways are provided between adjacent fins 46 and the long walls 34. Each end of the bench is provided with a plurality of holes 48 to allow air to pass therethrough. Filter elements 52 are located between end wall 36 and end cap 39 to reduce contamination within the hollow interior of the bench 40. Air is drawn into the interior of the bench 40 under urging of a fan 54 that draws air from the ambient conditions into holes 48 and exhausts air through slots 56 passing through the bottom wall 32 of the bench and into an exhaust cowling 58 (please see FIG. 6).

Similarly, the canopy 60 has an arcuate top cover 62 (concave towards the bench) and elongate side walls 64 terminated by end walls 66 which have the same removable attachment features that the bench has. In addition, the canopy 60 includes similar filters 72 which allow air to pass within the interior 74 of the canopy and be exhausted via slits 76 provided in the canopy cover 62 after having passed through the end wall 66 via holes 78. Specifically, filters 72 are replaceable by removing the end cap 89 (having foramen 49) from the end walls 66. The canopy is provided with fans 84 that lead from a cowling 82 in a manner similar to the bench. A clear cover 86 having air channeling fins 88 integrated therewith provide the channel ways for proper air flow so that the UV tubes 90 are maintained in a temperature controlled environment. The air flow is intended to assure that the UV tubes are provided with adequate ventilation so that they operate at their optimal temperature. A thermistor 81 is included in the exhaust cowling of both the bench and the canopy to regulate the air flow rate through the fans 84 to provide optimum temperature control, particularly after use of the device 10 to assure proper cool down.

FIG. 1 reflects further details on the manner in which the canopy 60 is attached to the other structure to form the tanning bed 10. As mentioned, the bench supports 20 include first and second upwardly and outwardly splayed legs 6. As shown in FIG. 1, each rearward leg 6 includes a hollow interior, square in section. The interior hollow receives a post 92 frictionally within the hollow of the legs 6 in the direction of the arrow A in FIG. 1. Two posts 92 are provided interconnected by a transverse member 94, shaped as an angle iron.

Figures 3, 3A, 3B:
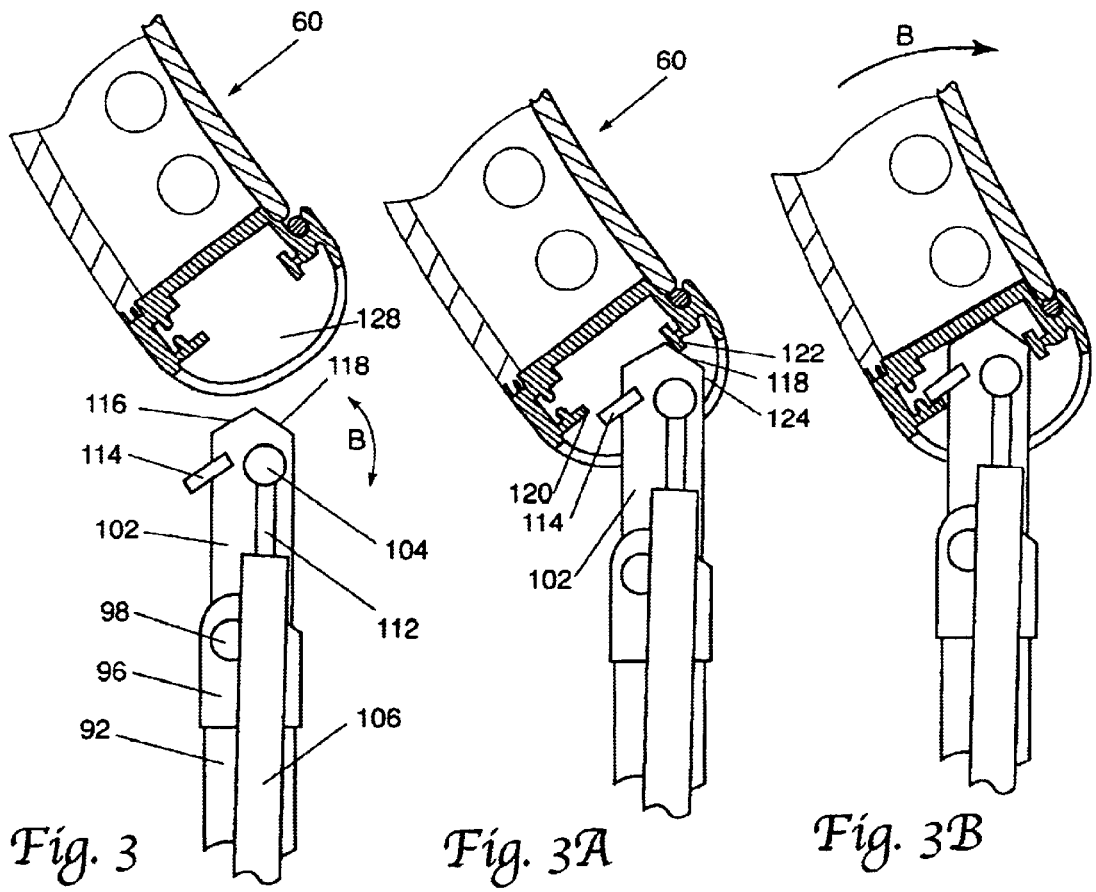
FIGS. 3, 3A, 3B and 3C detail the mounting protocol for installing the canopy to an underlying bench.
Figure 3C:
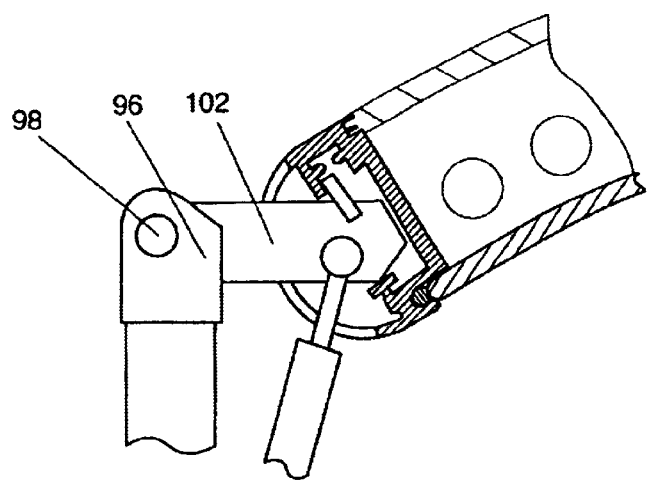
Figure 4:
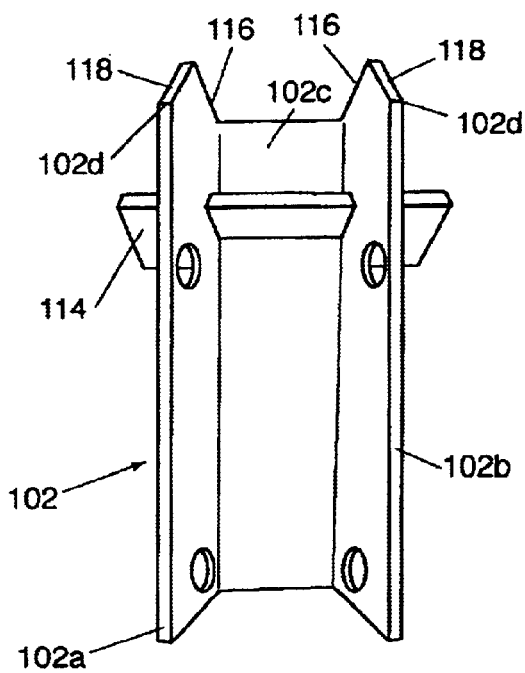
FIG. 4 is a front view of the FIGS. 3 link.
Figure 4A:
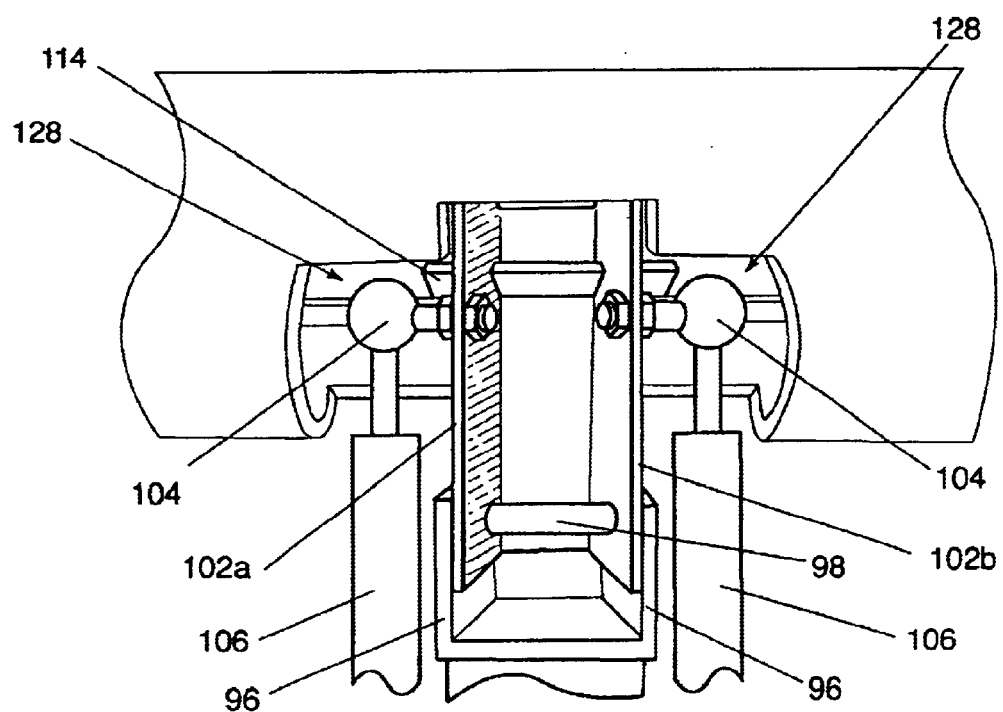
FIG. 4A shows the shocks attached thereto.

The upper ends of the posts 92 are detailed in FIGS. 3, 3A, 3B and 3C. Each post 92 supports a pair of gusset-like plates 96 that has a pivot 98 that supports a link 102, shown in FIG. 4. The link 102 is formed as two spaced parallel plates 102a, 102b united by a backwall 102c and moves along the direction of the arrow B shown in FIG. 3. The link 102 also includes one end 104 of a gas shock 106. Preferably, two gas shocks are on each link 102 on outside faces of plates 102a and 102b. Each gas shock 106 has a remote end attached on the post 92 adjacent the transverse member 94. The attachment is shown as a pivot 108. A telescoping rod portion 112 of the gas shock extends from the shock 106 as shown in FIG. 3. The link 102 also includes a catch member 114 on an end of the link 102 opposite from the pivot 98. The link 102 includes an inverted V-shaped upper end having a first surface 116 and a second surface 118. The first surface 116 is nearer the catch 114.

FIG. 3A shows the link 102 being received in a hollow 128 on the canopy 60. The hollow is defined by an aluminum molding of generally arcuate configuration having an abutment 120 that is to capture the latch 114 by having the latch rest on top of the abutment 120 as shown in the various FIG. 3 positions. In addition, the aluminum channel includes a bead 122 which frictionally resides against a terminus of the second surface 118 adjacent a front face 102d of the link plates 102a, 102b, just at one end of the V-shaped upper end. The structure allows for ready affixion and removal of the canopy 60 from the link 102. Each gas shock is placed within the path of heat flow emanating from the lamps 90. The hollow 128 helps to provide a heat trap near the gas shocks. The outside surface of the gas shocks conduct heat to its interior. As the gas shocks heat up, the temperature of the internal gas increases, resulting in greater internal pressure. This gives the gas shock a performance boost during use and makes the canopy actually easier to move between the first and second extreme positions by a tanner than when the shocks are cold.

Referring to FIG. 1, FIG. 5, FIG. 5A, FIG. 7 and FIG. 8, the mechanism by which the bench 40 attaches to the supports 20 can be explored. The rear leg 6 of the support 20 includes an L-shaped projection 132 having a tapered leading edge disposed in a horizontal plane, the taper 134 coming to a point to allow locating and inserting the projection 132 into a complementarily formed slit 138 on the backside rail 34 of the bench. Please see FIG. 8.

In addition, the front rail 34 of the bench 40 is secured by another slit 148 which receives a hook 142 located on a cradle strap 144 that extends between the forward leg 6 and the upper horizontal leg 4. A similar strap 128 is located between the rear leg 6 and the horizontal leg 4. These straps 128, 144 cradle and support the bench in its down position, and the latch mechanism 142 secures the bed in that at rest state. A tang 146 (FIG. 7) depends from the strap 144 and supports a pivot lever 148 coupled to the hook 142 and pinned via pivot 152 to the tang 146. The pivot 152 is offset to provide a cam-like locking action, and the hook 142 is pivoted to the pivot lever 148 via a pivot 154.

FIGS. 7 and 8 are also instructive in noticing how the cover 42 sets into the side rails 34 so that a smooth transition exists at the juncture. As shown in each of these drawings, gasket material 156 resides within a channel 158 formed in the side rails 34 on inner facing edges thereof so that the gasket 158 seats therewithin. The cover 42 is frictionally held between the two gaskets and is then urged to stay in this position to be tailored to accommodate the complemental curvature of the bench 40 as it extends along the top edges of the fins 46 and the ledge 162 formed adjacent the cover 42 on the interior portion of the side walls 34. This feature allows the cover 42 to be frictionally held with a close tolerance at the juncture where the side walls 34 come into contact with the cover 42 and is frictionally held there yet easy to replace or remove for access to the ultraviolet lights 90. Cover 42 is formed from acrylic and is of a thickness that allows it to be bent to form the arcuate shape supported on the elements recited above. The top cover 86 can be similarly retained.

Figure 5A:
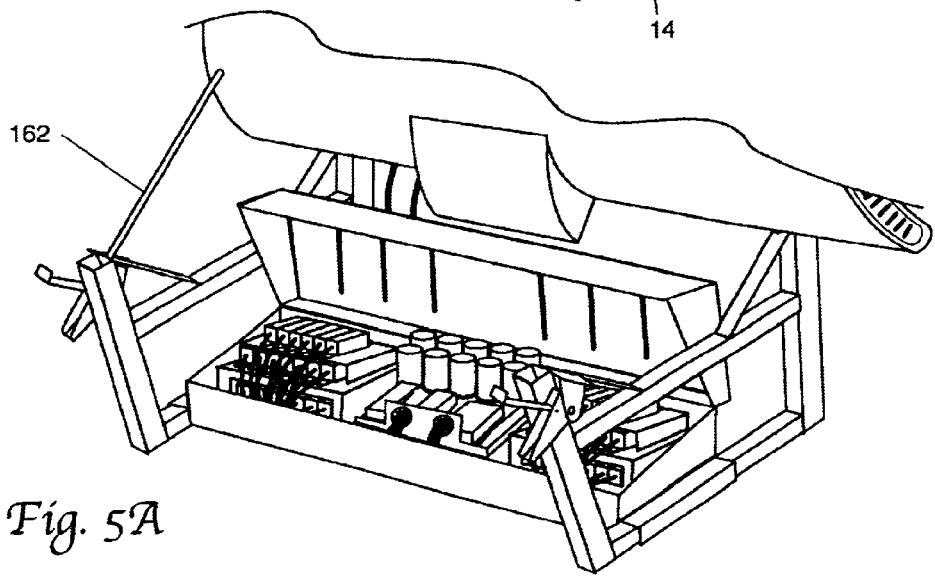

FIGS. 5 and 5A shows the platform 40 being held in an elevated position off of the straps 128 and 144 yet still adapted to pivot about the projection 134. A stand member 162 is interposed between the bottom surface 32 of the bench 40 and the forward leg 6 to prop the platform 40 in an elevated position. This allows access to the ballast assembly 30 which in FIG. 5A is shown open should it be necessary to remove any of the modules which are depicted in FIG. 2.

Figure 9:
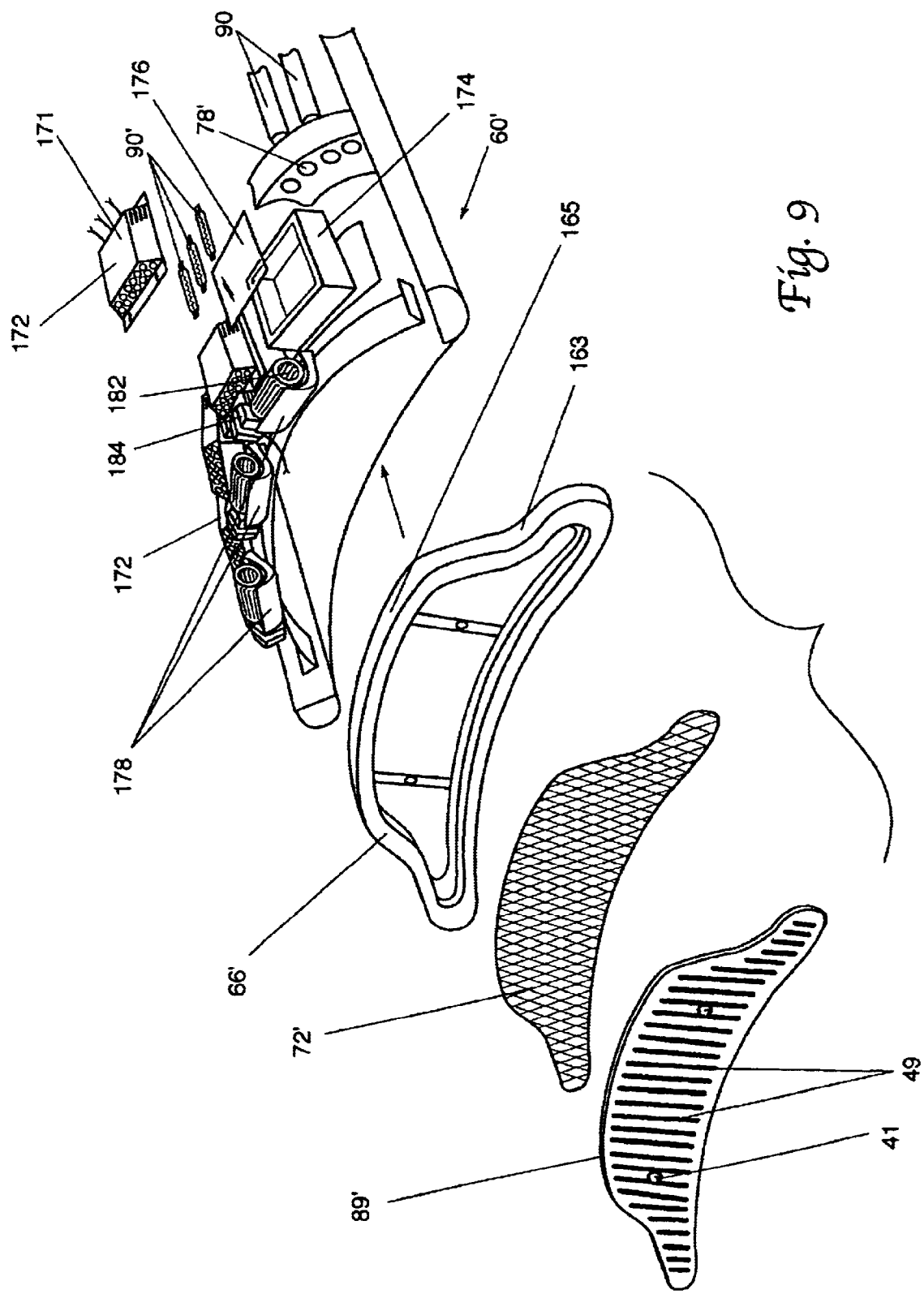
FIG. 9 is a view of a face tanner.

FIG. 9 shows a variation in a tanning canopy 60' and only the nonduplicative elements are illustrated. In this variation, a zone of increased ultraviolet radiation is provided oriented adjacent a face area of the user. Typically, one's face has a greater degree of resistance to tanning since it is exposed at all times, unlike other parts of the body. Thus, the face can withstand a greater degree of ultraviolet radiation. As shown in FIG. 9, the end wall 66', filter 72' and end cap 89' have been included with a raised boss 165 including a radiused transition area 163 to accommodate the modules 172 that house the higher intensity UV bulbs 90'. Clusters of as many as four of the high output UV bulbs 90' are located in each cluster 172, and each of which is constrained to operate within a box-shaped well 174 which secures to the inverted support tray 171 of module 172. A window 176 separates the user from the bulbs 90'. In addition, because of the additional heat generation, a plurality of fans 178 augment the air flow through this area. These fans 178 are preferably of the "cross blow" type with cages 182 driven by motors 184 to provide additional air flow. The air ventilation holes 78' have been shown along with the ultraviolet lights 90.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A tanning bed comprising in combination:
  a plurality of modules collectively defining components of said tanning bed, said components including a pair of spaced bench supports including a ballast housing interposed between said bench supports and means fixing said ballast housing to said bench supports in removable relationship thereto, wherein said bench supports cradle a bench in removable overlying relationship thereto, said bench provided with illumination means for tanning, and wherein said bench supports fasten to a canopy and a pair of posts project upwardly from said bench supports in frictional telescoping relationship, said posts including a pivot that supports a link operatively coupled to said canopy and adapted to allow said link and said canopy to move from a first open position wherein a tanner can lie on the bed to a second closed position where said canopy is in overlying relationship with respect to said bed and said tanner, and gas shock means operatively coupled with said link and said post in a path of heat radiation whereupon gas within said shock elevates in temperature upon utilization of said bed increasing the effectiveness of said gas shock; and
  said canopy operatively connected to said bench by removeable attachment means, said canopy provided with illumination means for tanning.

2. The bed of claim 1 wherein said link is received within a hollow of said canopy, said canopy including an abutment which captures a latch projecting from said link, said hollow including a bead which frictionally resides against a terminus of said link.

3. A tanning bed comprising in combination:
  a plurality of modules collectively defining components of said tanning bed, said components including bench supports, a bed, and a canopy, wherein said bench supports fasten to said canopy and a pair of posts project upwardly from said bench supports in frictional telescoping relationship, said posts including a pivot that supports a link operatively coupled to said canopy and adapted to allow said link and said canopy to move from a first open position wherein a tanner can lie on the bed to a second closed position where said canopy is in overlying relationship with respect to said bed and said tanner, gas shock means operatively coupled with said link and said post in a path of heat radiation whereupon gas within said shock elevates in temperature upon utilization of said bed increasing the effectiveness of said gas shock.

* * * * *